United States Patent [19]
Palmacci et al.

[11] Patent Number: 5,262,176
[45] Date of Patent: Nov. 16, 1993

[54] SYNTHESIS OF POLYSACCHARIDE COVERED SUPERPARAMAGNETIC OXIDE COLLOIDS

[75] Inventors: Stephen Palmacci, Walpole; Lee Josephson, Arlington, both of Mass.

[73] Assignee: Advanced Magnetics, Inc., Cambridge, Mass.

[21] Appl. No.: 694,636

[22] Filed: May 2, 1991

Related U.S. Application Data

[63] Continuation-in-part of Ser. No. 384,991, Jul. 28, 1989, abandoned, which is a continuation-in-part of Ser. No. 228,640, Aug. 4, 1988, abandoned, which is a continuation-in-part of Ser. No. 67,586, Jun. 26, 1987, Pat. No. 4,827,945, which is a continuation-in-part of Ser. No. 882,044, Jul. 3, 1986, Pat. No. 4,770,183, which is a continuation-in-part of Ser. No. 650,957, Feb. 5, 1991, Pat. No. 5,160,726, which is a continuation-in-part of Ser. No. 480,677, Feb. 15,1990, abandoned.

[51] Int. Cl.$^5$ .............. G01N 24/08; B01J 13/02; A61M 37/00; A61K 33/26
[52] U.S. Cl. .................. 424/9; 427/213.33; 128/653.4; 128/654; 600/12; 424/646; 648/403; 648/407
[58] Field of Search ............ 424/9, 646, 648; 427/213.33; 128/653.4, 654; 600/12; 428/403, 407

[56] References Cited

U.S. PATENT DOCUMENTS

| | | | |
|---|---|---|---|
| 4,101,435 | 7/1978 | Hasegawa et al. | 252/62.53 |
| 4,452,773 | 6/1984 | Molday | 424/1.1 |
| 4,628,037 | 12/1986 | Chagnon et al. | 436/526 |
| 4,675,173 | 6/1987 | Widder | 424/9 |
| 4,698,302 | 10/1987 | Whitehead et al. | 435/94 |
| 4,795,698 | 1/1989 | Owen et al. | 435/4 |
| 4,849,210 | 7/1989 | Widder | 424/9 |
| 4,863,715 | 9/1989 | Jacobsen et al. | 424/9 |
| 4,965,007 | 10/1990 | Yudelson | 252/62.53 |
| 5,091,206 | 2/1992 | Wang et al. | 427/2 |

FOREIGN PATENT DOCUMENTS 9001295 2/1990 PCT Int'l Appl. .
9001899 3/1990 PCT Int'l Appl. .

OTHER PUBLICATIONS

Bradley et al. (1989) Stroke 20 pp. 1032–1036.
Cerdan et al. (1989) Mag. Res. Med. 12 pp. 151–163.
Iannone et al. "Blood Clearance of Dextran Magnetite Particles Determined by a Non-Invasive in Vivo ESR Method," submitted to J. Mag. Res. Med. (1990).
Jones and Summerfield, in "The Liver: Biology and Pathobiology," I.M. Arias et al., eds., Raven Press, New York, 1988, pp. 683–704.
Josephson et al. (1990) Mag. Res. Imag. 8 pp. 637–646.
Magin et al. (1991) Mag. Res. Med. 20 pp. 1–16.
Pouliquen et al. (1989) Mag. Res. Imag. 7 pp. 619–627.
Renshaw et al. (1986) Mag. Res. Imag. 4 pp. 351–357.
Weissleder et al. (1990) Radiology 175 pp. 489–493.
Widder et al. (1987) AJR 148 pp. 399–404.

Primary Examiner—Glennon H. Hollrah
Assistant Examiner—Gary E. Hollinden
Attorney, Agent, or Firm—Bromberg & Sunstein

[57] ABSTRACT

In a method for the synthesis of a colloid including a superparamagnetic metal oxide coated with a polymer, an acidic solution of a metal salt and a polymer may be cooled, and then neutralized by the controlled addition of a cool solution of a base, and may then be converted, by the application of heat, to a homogenous superparamagnetic metal oxide colloid. According to a preferred embodiment, the polymer may be a polysaccharide. In a further embodiment of the invention, the polysaccharide may be dextran and the metal salt may be ferrous and ferric salts, which produces, according to the methods of the invention, a superparamagnetic iron oxide colloid with an extended plasma half-life.

44 Claims, 6 Drawing Sheets

SYNTHESIS OF POLYSACCHARIDE COVERED SUPERPARAMAGNETIC OXIDE COLLOIDS

CROSS REFERENCE TO RELATED APPLICATIONS

This application is a continuation-in-part of U.S. application Ser. No. 07/384,991 now abandoned, filed Jul. 28, 1989, which is a continuation-in-part of U.S. application Ser. No. 07/228,640, filed Aug. 4, 1988, now abandoned, which is a continuation-in-part of U.S. application Ser. No. 07/067,586, filed Jun. 26, 1987, now U.S. Pat. No. 4,827,945, which is, in turn, a continuation-in-part of U.S. application Ser. No. 06/882,044, filed Jul. 3, 1986, now U.S. Pat. No. 4,770,183. It is also a continuation-in-part of U.S. application Ser. No. 07/650,957, filed Feb. 5, 1991 now U.S. Pat. No. 5,160,726, which is a continuation-in-part of U.S. application Ser. No. 07/480,677, filed Feb. 15, 1990 now abandoned. These related applications are hereby incorporated herein by reference.

TECHNICAL FIELD

The present invention relates to methods for the synthesis of polysaccharide covered superparamagnetic iron oxide colloids.

BACKGROUND ART

A. Introduction

A wide variety of processes have been used in the synthesis of magnetic particles or colloids, which have often been used as MR contrast agents. Klaveness, U.S. Pat. No. 4,863,715; Owen, U.S. Pat. No. 4,795,698; Widder, U.S. Pat. No. 4,849,210; Hasegawa, U.S. Pat. No. 4,101,435; Groman, U.S. Pat. No. 4,827,945; Groman, U.S. Pat. No. 4,770,183; Menz, E. T., International Application, published under the Patent Cooperation Treaty, International Publication No. WO 90/01295, filed Aug. 3, 1989, published Feb. 22, 1990; and Lewis, International Application, published under the Patent Cooperation Treaty, International Publication No. WO 90/01899. These syntheses produce colloids that are heterogeneous and are rapidly removed from blood (or cleared) by phagocytic cells of the reticuloendothelial system (RES). These two features are undesirable in some important respects.

B. Problems with Heterogeneous Magnetic Colloids

The magnetic colloids and particles described previously are either too large or in some cases consist of too many differently sized particles, i.e. exhibit heterogeneity, to be sterilized by passage through a 220 nm filter. Filtration through a 220 nm filter meets the current legal requirement for sterility of parenteral pharmaceutical products. The inability to filter sterilize can result when a very small proportion of the colloidal material is large enough to be trapped on the filter, thereby blocking further filtration.

Heterogeneous colloids, or colloids composed of many subpopulations with a wide range of properties, can be difficult to characterize. Heterogeneity can obscure the detection of small atypical populations, such atypical populations being present either at the time of manufacture or developing with storage. With homogeneous colloids, a single population with a narrow range of properties comprises the colloid, and the detection of small, atypical subpopulations is facilitated. In the manufacture of superparamagnetic iron oxide colloids for injection into humans, atypical subpopulations of colloidal materials are considered to be potential sources of toxicity. Consequently, the ability to assure the absence of such subpopulations improves the quality of the colloid that can be produced.

Homogeneous colloids have previously been prepared by fractionation of heterogeneous colloids. For example, the heterogeneous colloid AMI-25 has been fractionated by Sepharose 4B column chromatography to yield four colloids of differing size, see Table I of Lewis, et al., International Application, published under the Patent Cooperation Treaty, International Publication No. WO 90/01899. AMI-25 is prepared according to Example 7.10 of U.S. Pat. No. 4,827,945. These experiments demonstrated that the size of superparamagnetic iron oxide colloids can play a role in controlling pharmacokinetics. As the size of the colloidal particle dropped below about 100 nm, clearance decreased, i.e. plasma half-life increased.

Dextran magnetite, prepared as described (Hasegawa, U.S. Pat. No. 4,101,435), is another example of a heterogeneous colloid. Dextran magnetite contains particles with diameters from 20 to 520 nm, median 160 nm. Like AMI-25, dextran magnetite has been subjected to size fractionation, with smaller fractions exhibiting longer blood half-lives. The overall preparation has a very short plasma half life of 3.5 minutes, the smallest fraction having a half-life of 19 minutes and the largest 0.9 minutes. Iannone, N. A. and Magin, R. L. et al., "Blood Clearance of Dextran Magnetite Particles Determined by a Non-Invasive In Vivo ESR Method" submitted to J. Mag. Res. Med.; Magin, R. L., Bacic G. et al. "Dextran Magnetite as a Liver Contrast Agent," (1991) Mag. Res. Med. 20 pp. 1–16.

In a synthesis described by Molday (U.S. Pat. No. 4,452,773) a heterogeneous colloid is produced, with the large aggregates being removed by centrifugation and discarded (column 8, line 40). The preparation of homogenous colloids from heterogeneous colloids is wasteful because unwanted colloidal material is discarded. In addition, the fractionation step itself is time consuming and expensive.

A second problem with the magnetic colloids and particles cited above is that after injection they exhibit rapid clearance by the tissues of the reticuloendothelial system (RES). Rapid clearance (short plasma half-life) limits the time the injected material is present in the blood pool of an animal. In some MR imaging applications, for example in the delineation of the capillary blood volumes of different parts of the brain, image contrast is enhanced by the presence of superparamagnetic iron oxide in the blood. Bradley et al. (1989) Stroke 20 pp. 1032–1036. A long plasma half-life lowers the dose of colloid needed and prolongs the time when a contrast enhanced MR image can be obtained.

The rapid clearance of prior art magnetic colloids or particles from the blood results from their uptake by the liver and spleen, the two major tissues of the RES. With rapidly cleared particles, typically about 90% of the injected material is extracted from blood by those two organs. Therefore rapid blood clearance limits the amount of colloid that can be targeted or delivered to cells other than phagocytes and tissues other than the liver and spleen.

There have been reports that surface chemistry can affect the fate of colloids after injection, for example results with a heterogenous colloid made with arabinogalactan. Josephson et al., (1990) Mag. Res.

Imag. 8 pp. 637-646; and Example 6.10.1 of Menz, E. T. International Application, published under the Patent Cooperation Treaty, International Publication No. WO 90/01295, filed Aug. 3, 1989, published Feb. 22, 1990. Similarly, there have been reports that attaching antibodies to iron oxide particles can achieve tissue specific uptake of the iron. Renshaw et al. (1986) Mag. Res. Imag. 4 pp. 351-357; and Cerdan et al., (1989) Mag. Res. Med. 12 pp. 151-163. However, such preparations are often heterogenous, cannot be filter sterilized, or show very substantial uptake by the liver and spleen. Uptake by the liver and spleen limits the amount of iron that can be targeted to other tissues.

SUMMARY OF THE INVENTION

The invention provides a method for the synthesis of a colloid including a superparamagnetic metal oxide covered with a polymer. According to a preferred embodiment of the invention, an acidic solution of a metal salt and a polymer may be cooled, and then neutralized by the controlled addition of a cool solution of a base, and may then be converted, by the application of heat, to a homogenous superparamagnetic metal oxide colloid. According to a further preferred embodiment of the invention, the polymer may be a polysaccharide. In one embodiment of the invention, an acidic solution of a polysaccharide and a metal salt may be cooled to between approximately 0° C. and approximately 12° C. The cooled solution may then be neutralized by the controlled addition of a base that has been cooled to between approximately 0° C. and approximately 12° C. The resulting solution may then be heated to between approximately 60° C. and approximately 100° C. for not less than approximately 30 minutes, to produce a homogenous superparamagnetic metal oxide colloid. The bases that may be utilized, in accordance with the invention, include ammonium hydroxide and sodium carbonate. In another embodiment of the invention, the polysaccharide may be dextran and the metal salt may be ferrous and ferric salts, which produces, according to the methods of the invention, a superparamagnetic iron oxide colloid with an extended plasma half-life.

BRIEF DESCRIPTION OF THE DRAWINGS

The foregoing features of the invention will be more readily understood by reference to the following detailed description taken with the accompanying drawings, in which.

DETAILED DESCRIPTION OF SPECIFIC EMBODIMENTS

A. General

The invention provides a method for the synthesis of a colloid including a superparamagnetic metal oxide covered with a polymer. According to a method of the invention, an acidic solution of a metal salt and a polymer may be provided, which is cooled, and then neutralized by the controlled addition of a cool solution of a base, to produce a weakly magnetic or nonmagnetic gel, which may then be converted, by the application of heat, to a homogenous superparamagnetic metal oxide colloid. The foregoing process of the invention may be referred to as a cold gelation process. In a preferred embodiment of the invention, the polymer may be a polysaccharide. In one embodiment of the invention, an acidic solution of a polysaccharide and a metal salt may be cooled to between approximately 0° C. and approximately 12° C. The cooled solution may then be neutralized by the controlled addition of a base that has been cooled to between approximately 0° C. and approximately 12° C., to produce a nonmagnetic or weakly magnetic gel. The resulting gel may then be heated to between approximately 60° C. and approximately 100° C. for not less than approximately 30 minutes, to produce a strongly magnetic or superparamagnetic homogenous metal oxide colloid. In accordance with a preferred embodiment of the invention, the bases which may be utilized include ammonium hydroxide and sodium carbonate. In a further embodiment of the invention, the polysaccharide may be dextran, and the metal salts may be ferrous and ferric salts, which produces, according to the methods of the invention, a superparamagnetic iron oxide colloid with an extended plasma half-life.

Figure 1:
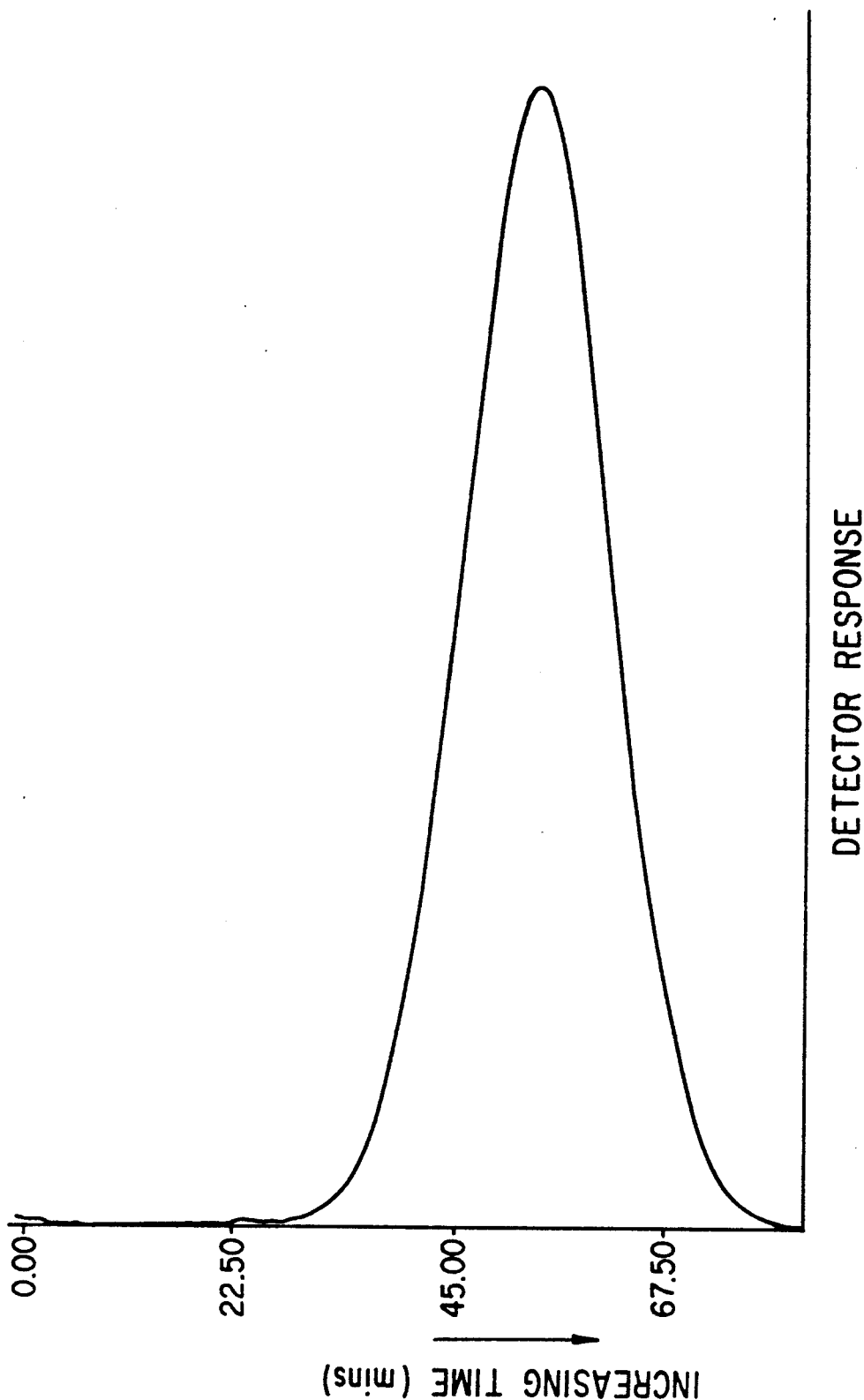
FIG. 1 is a Sepharose 2B gel filtration chromatogram, in accordance with Example 1.
Figure 2:
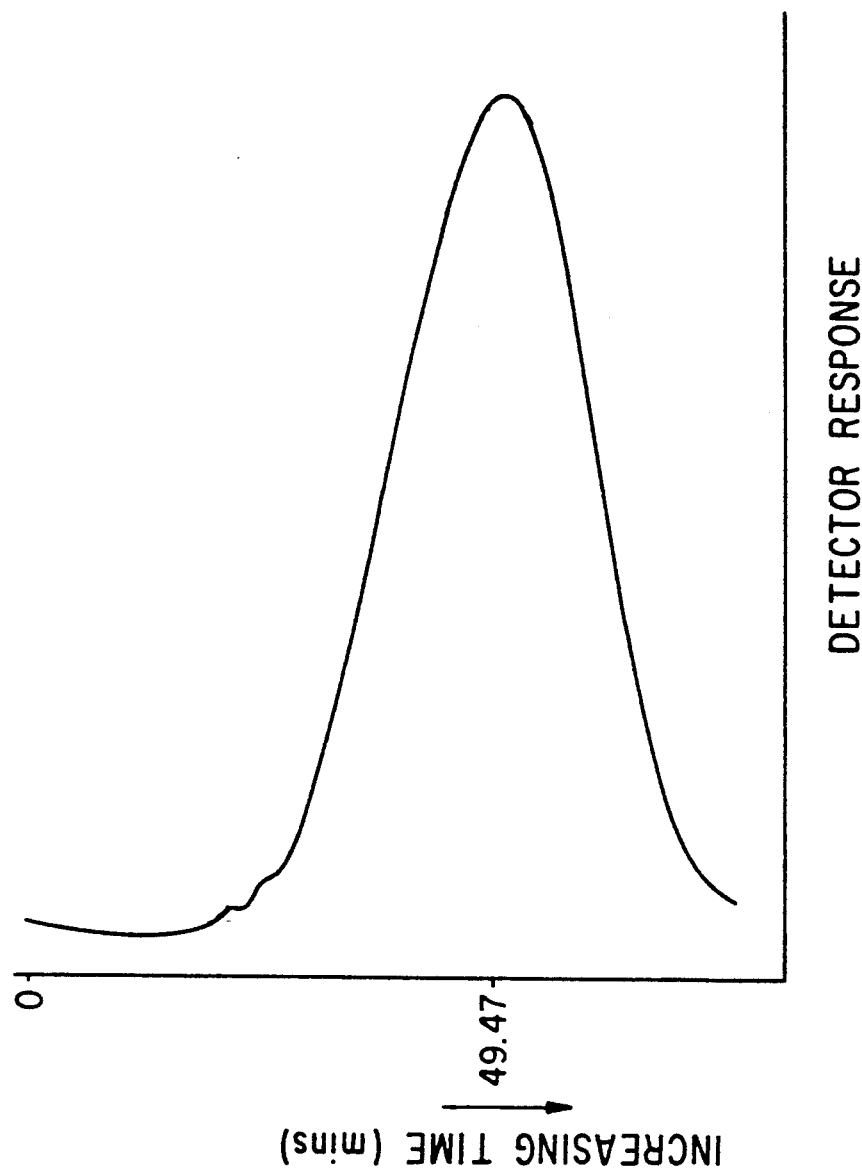
FIG. 2 is a Sepharose 2B gel filtration chromatogram, in accordance with Example 2.
Figure 3:
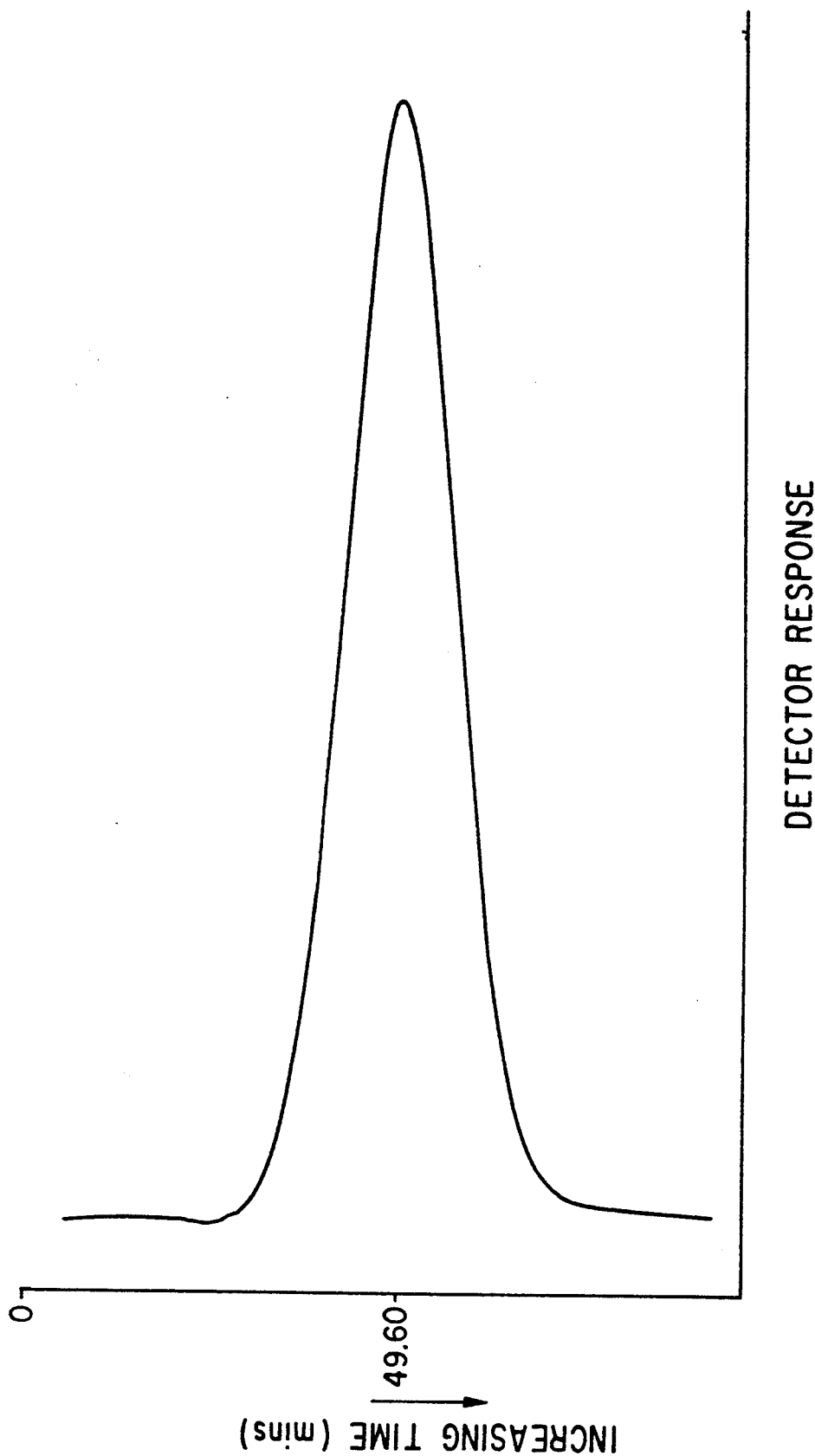
FIG. 3 is a Sepharose 2B gel filtration chromatogram, in accordance with Example 3.
Figure 4:
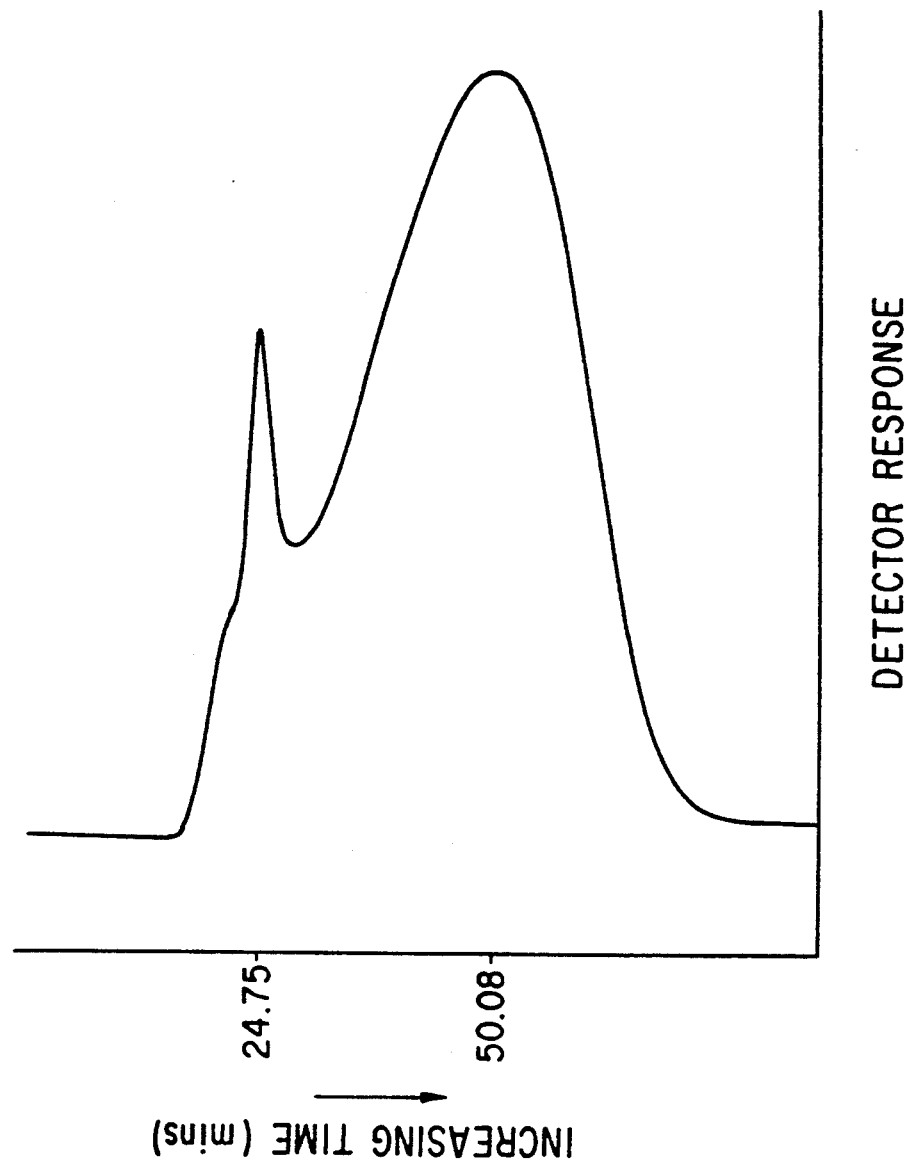
FIG. 4 is a Sepharose 2B gel filtration chromatogram of AMI-25.

The term "colloid" as used in this description and in the following claims includes any macromolecule or particle having a size less than about 220 nm. The colloids of the invention have substantially improved homogeneity, compared to previously described materials. Homogeneity is evident from the fact that the colloids of the invention show a single, well-defined peak by gel exclusion chromatography (FIGS. 1-3). In contrast, a colloid made by an earlier process, AMI-25, produces two peaks, which result from particle sizes as small as 5 nm and as large as several hundred nanometers (FIG. 4).

The process of the invention may yield colloids with a variety of sizes, though size depends somewhat on the technique used for size measurement. Size as measured by gel filtration (FIGS. 1-4) is the size obtained for the complex of polymer and metal oxide crystal in solution, or the hydrodynamic size. Hydrodynamic size depends largely on the number of iron crystals per particle and volume occupied by the polysaccharide covering. (See FIG. 6 for a schematic representation of particle architecture.) Size as measured by gel filtration is larger than size as seen by most electron microscopy techniques, in which only the electron dense superparamagnetic iron oxide (SPIO) core is visualized.

The process of the invention may be adjusted to yield homogenous colloids of various sizes, i.e. colloids comprised of varying numbers of iron oxide crystals per colloid particle. The colloid produced according to Example 1 has a hydrodynamic particle size of approximately 10-20 which includes even the largest, atypical colloid particles present. Because the 10-20 nm figure is a hydrodynamic size, and because the size of the component superparamagnetic iron oxide crystal in Example 1 is about 6 nm, that colloid is made up largely of particles which contain one crystal per particle. Thus the colloid from Example 1 is extremely well dispersed, i.e. is substantially a monodispersed iron oxide. On the other hand the colloid made according to Example 2 achieves its larger size by incorporating a larger number of crystals per colloidal particle. (Dextran T-10 is used as a polysaccharide covering in Examples 1 and 2, and does not account for the difference in particle sizes achieved by Examples 1 and 2.)

Figure 6B:
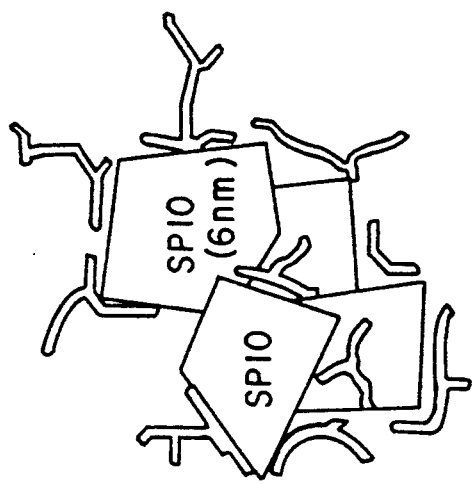
FIG. 6 is a schematic representation of two different sized dextran covered superparamagnetic iron oxide colloids.
Figure 6A:
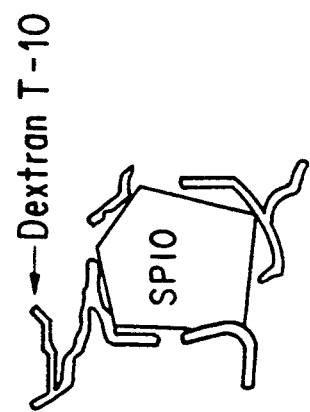

A schematic representation of the various size colloidal particles that may be produced by the invention is shown in FIG. 6. A monodispersed iron oxide crystal associated with T-10 dextran is shown in FIG. 6A; it will be a typical particle resulting from a synthesis such as that described in Example 1. A cluster of a small number of iron oxide crystals associated with dextran T-10 is shown in FIG. 6B; it will be a common colloidal particle resulting from a synthesis such as Example 2.

The process of the invention may be adjusted to yield homogenous colloids with hydrodynamic sizes down to about 300 kd (about 5 nm) or up to a maximum of about 10,000 kd (100-200 nm). In particular, the size of the colloid may be decreased by increasing the amount of polysaccharide relative to the amount of iron salts present for any synthesis. At the lower size limit, a pure preparation of monodispersed, polysaccharide covered superparamagnetic iron oxide colloid may be obtained. At the upper size limit, aggregates of superparamagnetic iron oxide crystals are produced, but the aggregates vary over a narrow size range. This narrow size range permits the colloids to be filter sterilized.

When dextran is used in the process, a colloid with a long plasma half-life after injection is obtained, and the colloid may be utilized as an MR contrast agent. The plasma half-lives and sizes of some of the better described colloids and particles used as MR contrast agents are compared with those made in accordance with the invention in Table 1. In some cases, direct, quantitative data on blood half-life is not provided, but a generally short blood half life may be inferred from the data indicating the rapid accumulation of particles in the liver and spleen. In the case of particles synthesized by the Molday method, only 20% of the injected iron remains in the blood two hours after injection, again indicating a short plasma half-life colloid (see FIG. 3 of Pouliquen et al., (1989) Mag. Res. Imag. 7 pp. 619–627), implying a very short half-life.

TABLE 1

Comparison Between the Current Invention and Other Materials Used as MR Contrast Agents

| Material | Size (nm) | $t_{\frac{1}{2}}$ (min) | Reference |
|---|---|---|---|
| Example 1 | 10–20 | 282 | |
| Example 2 | 30–50 | 154 | |
| Example 3 | 30–50 | <6 | |
| USPIO | 10–20 | 81 | Weissleder et al. Radiology 175:489 & 175:493; 1990. |
| DM | 160 | 3.5 | USP 4,101,435 see text |
| Dextran Microspheres | | short | USP 4,452,773 Pouliquen et al. Mag. Res. Imag. 7:619–627; 1989. |
| Albumin Microspheres | 1000–5000 | short | USP 4,675,173 Widder et al. AJR 148:399–404; 1987. |
| Starch Matrix | 100–500 | short | Fahlvik et al. Invest. Radiol. 25:113–120; 1990. |
| AMI-25 | 50–100 | 6 | USP 4,827,945 Weissleder et |

TABLE 1-continued

Comparison Between the Current Invention and Other Materials Used as MR Contrast Agents

| Material | Size (nm) | $t_{\frac{1}{2}}$ (min) | Reference |
|---|---|---|---|
| | | | al. Radiology 175:489 & 175:494; 1990. |

$t_{\frac{1}{2}}$ is the plasma half-life of the material in blood. For AMI-25, USPIO and Examples 1–3, plasma half-life was measured as described (Josephson et al., (1990) Mag. Res. Imag. 8 pp. 637–646).

In contrast, the plasma half-lives of the dextran covered superparamagnetic iron oxides of the current invention are greater than 100 minutes. When dextran is used in the cold gelation process of the invention, the surface of the superparamagnetic iron oxide is covered with dextran in a manner which extends the plasma half-life of the colloid. The ability of dextran to extend plasma half-life permits the dextran covered colloids of the invention to be distinguished from previously described magnetic materials involving dextran, see Table 2 below. This observation can be used as a test for distinguishing the dextran covered colloids of the invention from other materials, see below. The physiological mechanism by which dextran coverage extends the plasma half-life of the injected iron oxide is as follows.

After injection, previously described superparamagnetic iron oxide colloids (and nonmagnetic particles as well), are rapidly cleared because proteins in the blood called opsonins coat or deposit on the surface of the iron oxide. Opsonin coating marks the colloid for clearance by the phagocytic cells of the RES in a process termed nonimmune opsonization. Nonimmune opsonization and subsequent phagocytosis are the mechanism through which a variety of particles and colloids are cleared by the RES. The major plasma opsonin is a protein known as fibronectin. (For a discussion, see E. A. Jones and J. A. Summerfield, in "The Liver, Biology and Pathobiology," I. Arias, H. Popper, D. Schater and D. A. Schafritz, eds. Raven Press, New York, 1988, pp. 683–704).

We have found that a general feature of the cold gelation process is that the polysaccharide covering of the iron oxide can determine pharmacokinetics after injection. In the case of dextran, the covering extends plasma half-life (Table 2). When arabinogalactan replaces dextran in the cold gelation process (Example 3), as the polysaccharide covering, the polysaccharide again serves to determine the pharmacokinetics that result after injection. The arabinogalactan covered superparamagnetic iron oxide is removed from blood because arabinogalactan is recognized by the asialoglycoprotein receptor found on hepatocytes. The arabinogalactan covered colloid has a blood half-life of less than 10 minutes and is found in the only organ with hepatocytes, the liver. In contrast, the dextran covered colloids have blood half-lives of longer than 100 minutes (Table 1) and are found in the spleen as well as liver.

We have also found that a test of whether a colloid is dextran covered is provided by the response of the colloid to heat stress. When a superparamagnetic iron oxide colloid of the invention is heat stressed, the size of the colloid is unchanged but the dextran is dissociated from the surface of the iron oxide. Dextran dissociation can be seen directly by an increase in the amount of dialyzable, low molecular weight dextran present with the colloid (see Table 3 below). The functional consequence of dissociating the dextran from the surface of the superparamagnetic iron oxide is a decrease in plasma half-life. In Table 2, dextran covered colloids (Examples 1 and 2 of the current invention) and an earlier, superparamagnetic colloid (AMI-25) were heated, (121° C., 30 minutes) at iron concentrations between 5 and 50 mg/mL, at pH 8 in 5 mM citrate and 300 mM mannitol. It can be seen that the clearance of AMI-25 is rapid and unchanged by heat stress. This results because AMI-25 is not dextran covered, and its iron oxide reacts with opsonins and exhibits rapid blood clearance results, before or after heat stress. On the other hand, the clearance of the dextran covered colloids of the invention is normally slow and is dramatically increased by heat stress. This results because the dextran covering of these materials prevents opsonization and is removed or dissociated from the surface by heat stress. Further proof of the role of dextran in extending plasma half-life is provided when the dextran dissociation normally produced by heat treatment is blocked by crosslinking (see Table 3, below).

Thus, the terms "covered" or "covers", as used in this description and the following claims in connection with dextran or another polysaccharide or other polymer, mean the dextran or other polymer is associated with the surface of the superparamagnetic metal oxide in such a way that the polymer blocks opsonization and increases the plasma half-life of the metal oxide (except when the polymer is itself recognized by a cell receptor and permits the metal oxide to be internalized into the cell by receptor mediated endocytosis). When dextran is used as a polysaccharide in the cold gelation process, the resulting colloid has unique surface, i.e. is dextran covered, and unique function, i.e. long plasma half-life.

In a further embodiment, the colloids of the invention may be stabilized through procedures which result in a crosslinking of polysaccharides. In crosslinking, the colloid is treated with agents that react with two or more polysaccharide molecules on the surface of the iron oxide. As explained below, crosslinking results in a tighter association between the polysaccharide and the iron oxide.

Many agents with more than one reactive center can be used for crosslinking such as glutaraldehyde, disuccinimydyl suberate (DSS) and diethylenetriaminepentaacetic acid anhydride (DTPA anhydride). Agents used to activate polysaccharide particles for the immobilization of biological molecules frequently crosslink to a significant extent and can be used. Agents of this type include cyanogen bromide, ethylchloroformate and divinyl sulfone. The preferred crosslinking agent is epichlorohydrin. The dextran covered colloid prepared according to Example 1 is crosslinked with epichlorohydrin in Example 4.

The stabilizing effects of crosslinking are demonstrated when the colloid is subjected to heat stress in Table 3. The effect of crosslinking was measured as: (i) the ability of crosslinking to block the heat induced dissociation of dextran from the surface of the iron oxide and (ii) the ability of crosslinking to block the heat induced decrease in plasma half-life.

The colloid from Example 4, 11 mg/mL Fe, in 25 mM sodium citrate, pH 8, was heat stressed, (121° C. for 30 minutes). The association of dextran from the colloid is measured as the dextran that passes through a microconcentrator ultrafiltration membrane with a 100 kd cutoff (Amicon, Danvers, Mass.). The percentage of free dextran is the concentration of free dextran divided by the dextran concentration of the colloid before ultrafiltration (the free and bound fractions taken together).

With the noncrosslinked colloid, heat stress dissociates dextran from the surface of the iron oxide, as evident by the increase in free dextran from 5.6 to 28% of the total dextran. With the crosslinked colloid, an increase in free dextran from 5.6% to only 8% was obtained. This indicates that epichlorohydrin treatment results in a tighter association between the dextran and the iron oxide. When heat stressed, the crosslinked colloid does not show a decrease in plasma half-life.

These results indicate that crosslinking blocks the heat induced dextran dissociation, and the associated drop in plasma half-life. The ability of crosslinking to block both dextran dissociation and the drop in plasma half-life further supports the view that dextran covers the surface of the iron oxide, blocks nonimmune opsonization, and extends plasma half-life.

The colloids of the invention can be used as MR contrast agents or in other applications including but not limited to the magnetic fractionation (or sorting) of cells, immunoassay applications, gene assay applications and magnetically targeted drug delivery. The crosslinked colloids are particularly well suited to nonparenteral applications (e.g. cell sorting), because of their improved stability and because the metabolism and toxicity of the modified dextran need not be investigated.

TABLE 2

Test for Dextran Coverage of a Superparamagnetic Iron Oxide Colloid

| Material | $t_{\frac{1}{2}}$ (min) | Size (nm) | Dextran Covered |
|---|---|---|---|
| Example 1 | 282 | 10-20 | yes |
| Heated Example 1 | 99 | 10-20 | no |
| Example 2 | 154 | 30-50 | yes |
| Heated Example 2 | 36 | 30-50 | no |
| AMI-25* | 6 | 50-100 | no |
| Heated AMI-25* | 6 | 50-100 | no |

*Very heterogeneous colloid. Size is an estimate based on the volume median diameter by light scattering of typical preparations.

TABLE 3

Effect of Heat on Crosslinked and Non-Crosslinked Dextran Covered Superparamagnetic Iron Oxide Colloid

| Colloid | % Free Dextran | Heat Stress | Plasma $t_{\frac{1}{2}}$ (min) |
|---|---|---|---|
| I. Crosslinked Dextran Covered Colloid | | | |
| Example 4 | 5.6 | no | 495 |
| Example 4 | 8.6 | yes | 837 |
| II. Non-crosslinked Dextran Covered Colloid | | | |
| Example 1 (Table 2) | 5.6 | no | 282 |
| Example 1 (Table 2) | 28 | yes | 99 |

B. The Cold Gelation Process: General Procedure

The synthesis of superparamagnetic iron oxides by the cold gelation process in accordance with a preferred embodiment of the invention involves two steps. They are: (i) the neutralization of iron salts with base at between about 0° C. and about 12° C. to form a weakly magnetic or paramagnetic slurry or gel, and followed by, (ii) heating to convert the paramagnetic gel to a superparamagnetic colloid. Formation of a paramagnetic slurry in step (i) is a unique feature of the cold gelation process. The slurry formed is termed 'paramagnetic' by virtue because of the large amounts of paramagnetic iron it has incorporated, but it exhibits no discernable magnetic properties such as attraction to an external, hand held magnet.

In a preferred embodiment of the cold gelation process, a mixture of ferric and ferrous salts and a polysaccharide are dissolved in water. The mixture is chilled to below about 12° C., generally to between 2° and 4° C. A base is slowly added, which causes ionic iron to form a green gel or slurry of iron oxide. Ammonium hydroxide and sodium carbonate are the preferred bases. As the iron oxide develops in the cold, it forms under different conditions from those previously employed by others. Typically the heating step involves raising the temperature of the paramagnetic slurry to between about 60° C. and about 90° C. for at least about 0.5 hours. During the heating, the paramagnetic slurry is transformed from a green, weakly magnetic slurry to a black, strongly paramagnetic colloid.

After the heating step, the mixture contains in some proportion: (i) the superparamagnetic iron oxide colloid coated with polysaccharide; (ii) polysaccharide; (iii) trace soluble amounts of ionic iron and $NH_4Cl$. The mixture is then subjected to a fractionation step to separate all high molecular weight colloidal iron (>100 kd or kilodalton) from the low molecular polysaccharides, ionic iron, ammonia and chloride ions (<100 kd).

Figure 5:
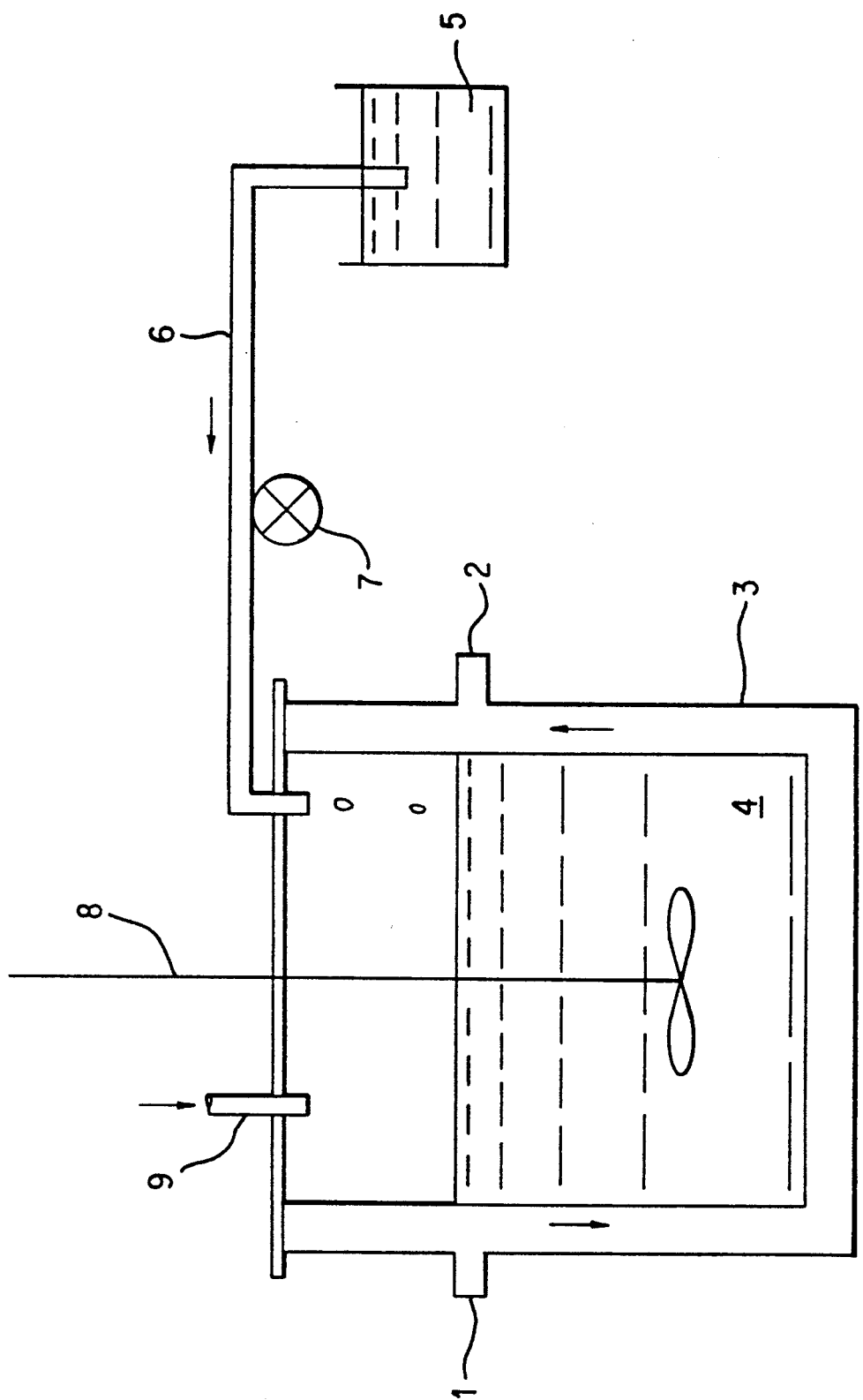
FIG. 5 is an illustration of a reactor for the cold gelation process of the foregoing examples.

The cold gelation process can be accomplished in different types of reactors, one of which is shown in FIG. 5. Here neutralization is accomplished by using a pump (7) to add base (5), through tube (6), to a jacketed, stirred reaction vessel containing stirrer (8) and a solution of iron salts and polysaccharide (4). The temperature is maintained at between about 0° C. and about 12° C., preferably at 2–4° C., by cold water flowing from inlet (1) through the jacket of the reactor (3) to outlet (2). Heating is accomplished by increasing the temperature of the water in the jacket to between about 80° C. and about 100° C. after the gelation step. As a result, the temperature of the non-magnetic slurry increases up to about 70° C. to about 80° C. over a period of about an hour. During this step the high magnetic or superparamagnetic, homogeneous colloid is formed. A nitrogen atmosphere is maintained by flushing with that gas through tube (9).

Solutions containing iron salts and dextran are passed through 220 nm filters to remove particulate matter and reduce the bioburden of the resulting colloid. Additional filtration steps can be performed during the process, for example before the ultrafiltration removes the excess polysaccharide. This further limits the bioburden and reduces the possible contamination of the final colloid with endodoxin. The weakly magnetic gel or slurry formed immediately after neutralization in the cold cannot be filtered.

By the choice of appropriate conditions, the cold gelation process can yield homogeneous colloids of differing sizes. Particularly important conditions include the ratios of three reactants (i.e. ferric ion, ferrous ion and polysaccharide), and the overall concentrations (i.e. amount of water added). For Example 1 a homogenous, dextran covered colloid of between 600 and 900 kd (between about 10 to 20 nm) is produced. (For a chromatogram, see FIG. 1.) In Example 2, a homogenous, dextran covered colloid of about 1,000 to 1,500 kd (between about 30–50 nm) is produced. (For a chromatogram see FIG. 2.) In Example 3, a homogenous arabinogalactan covered colloid of about the same size as Example 2 is produced (FIG. 3). For comparison the chromatogram of AMI-25, a heterogenous colloid made by an earlier process, is shown in FIG. 4.

The colloids made according to Examples 1 and 2 are dextran covered as indicated by the ability of heat stress to shorten their plasma half-life (Table 2). The arabinogalactan covered colloid made according to Example 3 has a very short plasma half-life because the arabinogalactan is recognized by the asialoglycoprotein receptor of hepatocytes. It is rapidly cleared from plasma by the action of this receptor.

For the production of reproducible colloids and highly magnetic colloids, the reaction of oxygen with ferrous ion must be minimized and controlled. Failure to control oxygen exposure can lead to uncontrolled oxidation of the ferrous ion to ferric ion, which can reduce the magnetic properties of the resulting colloid. The availability of oxygen can be minimized by covering the jacketed reactor (FIG. 5) and purging with an oxygen free gas, preferably nitrogen. In one embodiment, the oxygen content is minimized by purging a solution of ferric chloride and dextran with nitrogen for 10–24 hours. The solution is placed in the reactor and stirred, while water at 4° C. flows through the jacket of the reactor. This results in an oxygen free solution at the temperature of jacketed water. To this is added a solid form of a ferrous salt, which is dissolved just before neutralization. Nitrogen purging is conducted during the heating steps, but is omitted during the addition of volatile bases such as ammonium hydroxide. After the neutralization and heating steps, oxygen exposure and subsequent oxidation has little effect on the colloid, as discussed below.

C. Alternatives and Substitutions:

A series of substitutions and alternatives are within the scope and teachings of the invention. Some of these are given below.

As an alternative to the batchwise reactor shown in FIG. 5, the mixing between the cold base on the one hand and the cold solutions of iron salt and dextran on the other can be accomplished in a continuous reactor. A two channel pump withdraws each solution and causes then to mix at the juncture of a 'Y' tube. The resulting paramagnetic slurry (cold gel) can be heated by collecting it in one of two manners. It can be collected in a jacked reactor as shown in FIG. 5, or by pumping the solution through a coil surrounded by water at about 95° C. If a heating coil is used, it must be long enough to heat the paramagnetic slurry for at least about 30 minutes, before the product exits the outlet of the heating coil.

Polysaccharides that can be used in conjunction with the cold gelation process include the dextrans, the arabinogalactans, dextrins, hydroxyethyl starches, mannans, galactans, sulfated dextrans and diethylaminodextrans. Polymers other than polysaccharides can be used, if they meet the requirements of the cold gelation process (as currently understood). The polymer must be stable to the acid environment required to keep ferric ion in solution, which is below pH 3, and the polymer must withstand the stress of the heating step, and must not bind ferric or ferrous ions, inhibiting the formation of iron oxide upon base addition. The polymer must also adsorb to the iron oxide surface.

Metals other than iron can be incorporated into the colloid by adding them as salts before the neutralization step. In particular $Co^{2+}$ or $Mn^{2+}$ can partially or completely replace $Fe^{2+}$. Like iron, these metals have a biological function and minimal toxicity. Sodium carbonate, prepared as a 26% w/w solution of the monohydrate salt, can be used instead of ammonium hydroxide.

Ultrafiltration is used to separate free polysaccharide from the polysaccharide covered superparamagnetic iron oxide colloid. The cutoff of the ultrafiltration membrane must be such that the polysaccharide is removed in the filtrate and the polysaccharide covered superparamagnetic colloid is retained. For the polysaccharides used in the examples below, an ultrafiltration membrane with a 100 kd or 300 kd cutoff is satisfactory. Ultrafiltration is the preferred technique for this separation step, but other practical methods include centrifugation, and gel permeation chromatography.

After the heating step, which forms the homogeneous superparamagnetic iron oxide colloid from nonmagnetic slurry, the ferrous iron exists within a magnetite or gamma ferric oxide type of crystal. Both these oxides of iron have similar magnetic properties. Consequently at this stage, complete oxidation of magnetite to gamma ferric oxide ($Fe^{2+}$ to $Fe^{3+}$) produces little change in the magnetic properties of the colloid. Oxidation can be accomplished by exposing of the colloid to oxidizing agents such as $H_2O_2$ at temperatures such as 25–50° C. and for incubation periods of between 10 and 50 hours. The resulting colloid will be the red brown color of gamma ferric oxide (gamma $Fe_2O_3$) rather than the brown or black of magnetite ($Fe_3O_4$), which contains ferrous ion ($Fe^{2+}$).

The colloids of the invention may be lyophilized and reconstituted without a change in their size distribution and without the formation of particulates. To achieve maximal stability for the colloid, excipients such as dextran or sodium citrate can be added.

The alternative to filter sterilization (discussed in part B of Background Art above) is terminal sterilization, which involves subjecting the colloid to high temperature (e.g. 30 minutes, 121° C.). Terminal sterilization meets the legal requirement for sterility of parenteral products. However, we have found that terminal sterilization produces unwanted effects on magnetic colloids and particles. Terminal sterilization can yield a colloid that produces a drop in blood pressure after injection. (See Table 1 of U.S. patent application Ser. No. 07/480,677.) This is a highly unwanted adverse reaction and even a low incidence of such reactions can prevent the regulatory approval required for sale of a pharmaceutical. Hence, the procedures of the present invention are also viewed as important to achieving sterilization without risk of increased toxicity.

D. Further Chemistry on the Polysaccharide Covered Colloids of the Invention

Further chemistry can be conducted on the dextran covered colloids of the invention, either prepared without crosslinking (see Examples 1 and 2) or stabilized with crosslinking (see Example 4). Since both types of dextran covered colloids have long plasma half-lives, the iron they possess can be directed or targeted to cells or tissues by the attachment of some antibodies, proteins, peptides, steroids, binding proteins or other materials to the dextran. The long plasma half-life permits the efficient targeting of superparamagnetic iron crystals to cells possessing antigens and receptors. The attachment of proteins to dextran of a magnetic iron oxide colloid has been described by Molday in U.S. Pat. No. 4,452,773; however, the iron oxide colloids prepared by the Molday method have a short blood half-life (see above and Table 2). As explained above, this is due to rapid clearance of injected iron by the phagocytes of the liver and spleen, and reduces the amount of iron that can be targeted to other sites. Thus the surface derivation of Molday type iron oxides does not yield an approach well suited for the targeting of iron to cells after injection.

EXAMPLES

Example 1

A Small Dextran Covered Colloid

One thousand and five milliliters of a 0.2 micron filtered aqueous solution of 450 grams of dextran, T-10, and 31.56 grams (116.76 mmoles) of ferric chloride hexahydrate is cooled to 2–4° C. To the above cooled mixture is added a freshly prepared (15–30 minutes) 0.2 micron filtered aqueous solution containing 12.55 gram (63.13 mmoles) of ferrous chloride tetrahydrate dissolved in water to a total volume of 43 milliliters. While being rapidly stirred the above acidic solution is neutralized by the dropwise addition of 45 milliliters of 2–4° C. cooled 28–30% ammonium hydroxide solution. The greenish suspension is then heated to between 75° and 85° C. over a one hour heating interval. The mixture is maintained in this temperature range for 75 minutes while stirring constantly.

The ammonium chloride along with excess dextran and ammonium hydroxide are removed by ultrafiltration on a 2 liter, CH-2 apparatus (Amicon, Inc., Danvers, Mass.) equipped with 300 kd hollow fiber cartridges. After about six washes the eluent is found to be free of all contaminants. The colloidal product is concentrated by ultrafiltration (<40 mg/ml) and 0.2 micron filtered. The resulting colloid exhibits a single peak of roughly 750 kd by gel chromatography on Sepharose 2B, which corresponds to a size of roughly 10–20 nm and molecular weight of between 600 and 900 kd. This indicates a homogenous colloid has been produced (FIG. 1).

The colloid has a susceptibility of greater than $25,000 \times 10^{-6}$ (c.g.s) per gram Fe which indicates the iron is superparamagnetic. (See Josephson et al., (1990) Mag. Res. Imag. 8 pp. 637–646, for details of susceptibility measurement. Paramagnetic iron would have a susceptibility of less than 5,000 in similar units.) The colloid is dextran covered and has a plasma half-life of greater than 200 minutes (Table 2).

Example 2

A Large Dextran Covered Colloid

Three hundred and eighty one milliliters of a 0.2 micron filtered aqueous solution of 170.5 grams of dextran, T-10, and 31.56 grams (116.76 mmoles) of ferric chloride hexahydrate is cooled to 2–4° C. To the above cooled mixture is added a freshly prepared (15–30 minutes) 0.2 micron filtered aqueous solution containing 12.55 grams (63.13 mmoles) of ferrous chloride tetrahydrate dissolved to a total volume of 43 milliliters. While being rapidly stirred the above acidic solution is neutralized by the dropwise addition of 2–4° C. cooled 28–30% ammonium hydroxide solution. The greenish suspension is then heated to between 75° and 85° C. over a one hour heating interval. The mixture is maintained in this temperature range for 75 minutes while stirring constantly.

The ammonium chloride along with excess dextran and ammonium hydroxide are removed by ultrafiltration on a 2 liter, CH-2 apparatus (Amicon, Inc., Danvers, Mass.) equipped with 300 kd hollow fiber cartridges. After about six washes the eluent is found to be free of all contaminants. The colloidal product is concentrated by ultrafiltration (<40 mg/ml) and is subsequently passed through filters of decreasing porosity of 800 nm, 450 nm and 220 nm.

The resulting colloid exhibits a single peak of roughly 1,000 to 1,500 kd by gel chromatography on Sepharose 2B, which corresponds to a size of roughly 30–50 nm, and a homogenous colloid is produced, as shown in FIG. 2. The colloid has a susceptibility of greater than $25,000 \times 10^{-6}$ (c.g.s) per gram Fe which indicates the iron is superparamagnetic. The colloid has plasma half-life of greater than 100 minutes and is dextran covered (Table 2).

Example 3

An Arabinogalactan Covered Colloid

Thirteen hundred milliliters of a 0.2 micron filtered aqueous solution of 325 grams of purified larch wood arabinogalactan and 24.25 grams (89.72 mmoles) of ferric chloride hexahydrate is cooled to 2–4° C. To the above cooled solution is added a freshly prepared (15–30 minutes) 0.2 micron filtered aqueous solution containing 18.84 grams (89.72 mmoles) of ferrous chloride tetrahydrate dissolved in water to a total volume of 33.3 milliliter. While being rapidly stirred, the above acidic solution is neutralized by the dropwise addition of 49.7 milliliters 2–4° C. cooled 28–30% ammonium hydroxide solution. The resultant greenish suspension is then heated to 85–90° C. over a one hour heating interval. The mixture is maintained in this temperature range for 75 minutes while stirring constantly.

The ammonium chloride along with excess arabinogalactan and ammonium hydroxide are removed by ultrafiltration on a 2 liter, CH-2 apparatus (Amicon, Inc., Danvers, Mass.) equipped with 300 kd hollow fiber cartridges. After about six washes the eluent is found to be free of all contaminants. The colloid product is concentrated by ultrafiltration (<40 mg/ml) and is subsequently passed through filters of decreasing porosity of 800 nm, 450 nm and 220 nm.

The resulting colloid exhibits a single peak of roughly 1,000 to 1,500 kd by gel chromatography on Sepharose 2B, which corresponds to a size of roughly 30–50 nm. A homogenous colloid has been produced, as shown in FIG. 3. The colloid has a susceptibility of greater than $25,000 \times 10^{-6}$ (c.g.s) per gram Fe which indicates the iron is superparamagnetic. The colloid has a plasma half-life of less than 10 minutes (Table 2), because of receptor mediated uptake by the asialoglycoprotein receptor.

Example 4

Crosslinking a Dextran Covered Colloid

The dextran covered colloid was prepared essentially according to Example 1. In a fume hood, to 20 milliliters of colloid (12 mmoles Fe) is added 100 milliliters of 5M NaOH, 40 milliliters distilled water and 40 milliliters epichlorohydrin. Some gas release occurs. The mixture is incubated at room temperature for about 24 hours with shaking to promote interaction of the organic phase (epichlorohydrin) and aqueous phase which includes the dextran covered colloid. Epichlorohydrin is removed by placing the colloid in a dialysis bag and dialyzing against 20 changes of distilled water of 20 liters each.

The size and magnetic properties of the colloid are unaffected by the this treatment and are those described by Example 1. The dextran of the crosslinked colloid is not dissociated by high temperature treatment that dissociates dextran from the surface of the parent dextran covered colloid (Table 3).

What is claimed is:

1. An improved method for obtaining an in vivo MR image of an organ or tissue of a human or animal subject, of the type including administering to such subject as a contrast agent to enhance such MR image an effective amount of a colloid including homogeneous superparamagnetic metal oxide particles dispersed in a physiologically acceptable carrier, wherein the colloid is synthesized by associating superparamagnetic metal oxide particles with a polymer in such a way that the polymer covers the superparamagnetic metal oxide particles and the polymer covering blocks opsominzation.

2. A method according to claim 1, wherein the polymer is a polysaccharide.

3. A method according to claim 1, further comprising crosslinking the polymer.

4. A method according to claim 2, further comprising crosslinking the polysaccharide.

5. A method according to claim 4, wherein the polysaccharide is dextran; and
    wherein the dextran is crosslinked with a crosslinking agent selected from the group consisting of epichorohydrin, glutaraldehyde, disuccinimydyl suberate, diethylenetriaminepentaacetic acid anhydride, cyanogen bromide, ethylchloroformate and divinyl sulfone.

6. A method according to claim 2, wherein the polysaccharide is dextran.

7. A method according to claim 6, wherein the colloid has a plasma half-life that is greater than approximately 20 minutes.

8. A method according to claim 1, wherein the synthesis of the colloid includes:
   (i) providing an acidic solution including a metal salt and the polymer;
   (ii) cooling the solution, obtained in step (i);
   (iii) neutralizing the solution, obtained in step (ii), by the controlled addition of a cool solution of a base; and
   (iv) heating the solution, obtained in step (iii), to obtain the homogenous superparamagnetic metal oxide colloid.

9. A method according to claim 8, wherein the polymer is a polysaccharide.

10. A method according to claim 9, wherein the polysaccharide is dextran.

11. A method according to claim 10, wherein the acidic solution, provided in step (i), includes a metal salt selected from the group consisting of
    (a) ferric salts;
    (b) ferrous salts; and
    (c) ferrous and ferric salts;
    wherein the ratio of the amount of dextran to the amount of metal salts, utilized in step (i), is approximately 10:1 by weight; and
    wherein the colloid, obtained in step (iv), is a superparamagnetic iron oxide colloid that includes a core consisting substantially of a single crystal of iron oxide.

12. A method according to claim 10, wherein the acidic solution, provided in step (i), includes a metal salt selected from the group consisting of
(a) ferric salts;
(b) ferrous salts; and
(c) ferrous and ferric salts;
wherein the ratio of the amount of dextran to the amount of metal salts, utilized in step (i), is approximately 4:1 by weight; and
wherein the colloid, obtained in step (iv), is a superparamagnetic iron oxide colloid that includes a core consisting substantially of a range of 1–4 crystals of iron oxide.

13. A method according to claim 10, wherein the colloid has a plasma half-life that is greater than approximately 20 minutes.

14. A method according to claim 8, further comprising, after step (iv):
(v) crosslinking the polymer.

15. A method according to claim 9, further comprising, after step (iv):
(v) crosslinking the polysaccharide.

16. A method according to claim 15, wherein the polysaccharide is dextran; and
wherein the step of crosslinking the dextran is performed with a crosslinking agent selected from the group consisting of epichorohydrin, glutaraldehyde, disuccinimydyl suberate, diethylenetriaminepentaacetic acid anhydride, cyanogen bromide, ethylchloroformate and divinyl sulfone.

17. A superparamagnetic metal oxide colloid comprising: a superparamagnetic metal oxide associated with a polymer in such a way that the polymer covers the superparamagnetic metal oxide and the polymer covering blocks opsominzation.

18. A colloid according to claim 17, wherein the polymer is a polysaccharide.

19. A colloid according to claim 17, wherein the polymer is crosslinked.

20. A colloid according to claim 18, wherein the polysaccharide is crosslinked.

21. A colloid according to claim 20, wherein the polysaccharide is dextran; and
wherein the dextran is crosslinked with a crosslinking agent selected from the group consisting of epichorohydrin, glutaraldehyde, disuccinimydyl suberate, diethylenetriaminepentaacetic acid anhydride, cyanogen bromide,, ethylchloroformate and divinyl sulfone.

22. A colloid according to claim 17, wherein the colloid is synthesized by:
(i) providing an acidic solution including a metal salt and the polymer;
(ii) cooling the solution, obtained in step (i);
(iii) neutralizing the solution, obtained in step (ii), by the controlled addition of a cool solution of a base; and
(iv) heating the solution, obtained in step (iii), to obtain the superparamagnetic metal oxide colloid.

23. A colloid according to claim 22, wherein the polymer, is a polysaccharide.

24. A colloid according to claim 23, wherein the polysaccharide is selected from the group consisting of arabinogalactan, dextran, hydroxyethyl starch, dextrin, mannan galactan, sulfated dextran and diethylaminodextran.

25. A colloid according to claim 22, wherein step (ii) includes the step of cooling the solution to between approximately 0° C. and approximately 12° C.; and
wherein step (iv) includes the step of heating the solution to between approximately 60° C. and approximately 100° C., for not less than approximately 30 minutes, to obtain the superparamagnetic metal oxide colloid.

26. A colloid according to claim 25, wherein the polymer is a polysaccharide.

27. A colloid according to claim 26, wherein the acidic solution, provided in step (i), includes a metal salt selected from the group consisting of
(a) ferric salts;
(b) ferrous salts; and
(c) ferrous and ferric salts; and
wherein, in step (iv), a superparamagnetic iron oxide colloid is obtained.

28. A colloid according to claim 27, wherein the polysaccharide is selected from the group consisting of arabinogalactan, dextran, hydroxyethyl starch, dextrin, mannan, galactan, sulfated dextran and diethylaminodextran.

29. A colloid according to claim 26, wherein the colloid is capable of interacting with a cell receptor and undergoing receptor mediated endocytosis into a specific population of cells.

30. A colloid according to claim 29, wherein the polysaccharide is arabinogalactan and wherein the cells are hepatocytes.

31. A colloid according to claim 29, wherein the plasma clearance of the colloid is inhibited by asialoglycoproteins.

32. A colloid according to claim 26, wherein the polysaccharide is dextran.

33. A colloid according to claim 32, wherein the colloid has a plasma half-life that is greater than approximately 20 minutes.

34. A colloid according to claim 27,
wherein the polysaccharide is dextran;
wherein the ratio of the amount of dextran to the amount of metal salts, utilized in step (i), is approximately 10:1 by weight; and
wherein the colloid, obtained in step (iv), includes a core consisting substantially of a single crystal of iron oxide.

35. A colloid according to claim 27,
wherein the polysaccharide is dextran;
wherein the ratio of the amount of dextran to the amount of metal salts, utilized in step (i), is approximately 4:1 by weight; and
wherein the colloid, obtained in step (iv), includes a core consisting substantially of a range of 1–4 crystals of iron oxide.

36. A colloid according to claim 25, wherein the colloid is an MR contrast agent.

37. A colloid according to claim 36, wherein the polymer is a polysaccharide.

38. A colloid according to claim 37, wherein the polysaccharide is selected from the group consisting of arabinogalactan, dextran, hydroxyethyl starch, dextrin, mannan, galactan, sulfated dextran and diethylaminodextran.

39. A colloid according to claim 25, wherein the synthesis of the colloid further comprises, after step (iv):
(v) crosslinking the polymer.

40. A colloid according to claim 26, wherein the synthesis of the colloid further comprises, after step (iv):

(v) crosslinking the polysaccharide

41. A colloid according to claim 40, wherein the polysaccharide is dextran; and wherein the dextran is crosslinked with a crosslinking agent that is selected from the group consisting of epichorohydrin, glutaraldehyde, disuccinimydyl suberate, diethylenetriaminepentaacetic acid anhydride, cyanogen bromide, ethylchloroformate and divinyl sulfone.

42. A colloid according to claim 39, wherein the colloid is an MR contrast agent.

43. A colloid according to claim 40, wherein the colloid is an MR contrast agent.

44. A colloid according to claim 41, wherein the colloid is an MR contrast agent.

* * * * *

UNITED STATES PATENT AND TRADEMARK OFFICE
CERTIFICATE OF CORRECTION

PATENT NO. : 5,262,176
DATED : November 16, 1993
INVENTOR(S) : Palmacci, Josephson, Groman It is certified that error appears in the above-indentified patent and that said Letters Patent is hereby corrected as shown below:

col. 1, line 5: immediately after the title of the invention, the following sentence should be added:

"Under 35 USC 202(c)(6) the government may have certain rights in the inventions claimed in this patent, based upon support that it provided to the applicants and their assignee."

Signed and Sealed this

Thirty-first Day of October 1995

Attest:

BRUCE LEHMAN

Attesting Officer

Commissioner of Patents and Trademarks